US006610271B2

(12) United States Patent
Wermeling

(10) Patent No.: US 6,610,271 B2
(45) Date of Patent: Aug. 26, 2003

(54) SYSTEM AND METHOD FOR INTRANASAL ADMINISTRATION OF LORAZEPAM

(75) Inventor: Daniel P. Wermeling, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/790,199

(22) Filed: Feb. 20, 2001

(65) Prior Publication Data

US 2001/0055571 A1 Dec. 27, 2001

Related U.S. Application Data

(63) Continuation-in-part of application No. 09/569,125, filed on May 10, 2000, now abandoned.

(51) Int. Cl.[7] .......................... A61N 25/02; A61K 9/00; A61K 1/55; A61L 9/04
(52) U.S. Cl. .......................... 424/43; 514/219; 514/220
(58) Field of Search ............................ 424/401, 44, 43; 514/219, 220

(56) References Cited

U.S. PATENT DOCUMENTS

| 4,950,664 | A | * | 8/1990 | Goldberg | .................... | 514/219 |
|---|---|---|---|---|---|---|
| 5,132,114 | A | * | 7/1992 | Stanley et al. | ............... | 424/440 |
| 5,307,953 | A | * | 5/1994 | Regan | .......................... | 222/82 |
| 5,397,771 | A | * | 3/1995 | Bechgaard et al. | ............. | 514/2 |
| 5,428,006 | A | * | 6/1995 | Bechgaard et al. | ............. | 514/3 |
| 5,693,608 | A | * | 12/1997 | Bechgaard et al. | ............. | 514/2 |
| 6,015,797 | A | * | 1/2000 | Camborde et al. | ............. | 514/46 |
| RE36,744 | E | * | 6/2000 | Goldberg | ..................... | 514/219 |
| 6,193,985 | B1 | * | 2/2001 | Sonne | ......................... | 424/400 |
| 6,228,383 | B1 | * | 5/2001 | Hansen et al. | ............... | 424/407 |
| 6,255,502 | B1 | * | 7/2001 | Penkler et al. | ............... | 552/549 |
| 6,274,635 | B1 | * | 8/2001 | Travis | ......................... | 514/885 |

FOREIGN PATENT DOCUMENTS

WO 90/02737 * 3/1990

* cited by examiner

*Primary Examiner*—Sreeni Padmanabhan
*Assistant Examiner*—Lauren Q. Wells
(74) *Attorney, Agent, or Firm*—Milton Springut; William D. Schmidt; Kalow & Springut LLP

(57) ABSTRACT

A therapeutic composition of lorazepam and its pharmaceutically acceptable derivatives are provided for intranasal administration of at least one predetermined volumetric unit dose in the form of a spray by means that delivers one or more therapeutically prescribed unit doses that are highly accurate as to the volume discharged and which leave no significant quantity of the composition in the delivery means.

28 Claims, 1 Drawing Sheet

SYSTEM AND METHOD FOR INTRANASAL ADMINISTRATION OF LORAZEPAM

Figure 1:
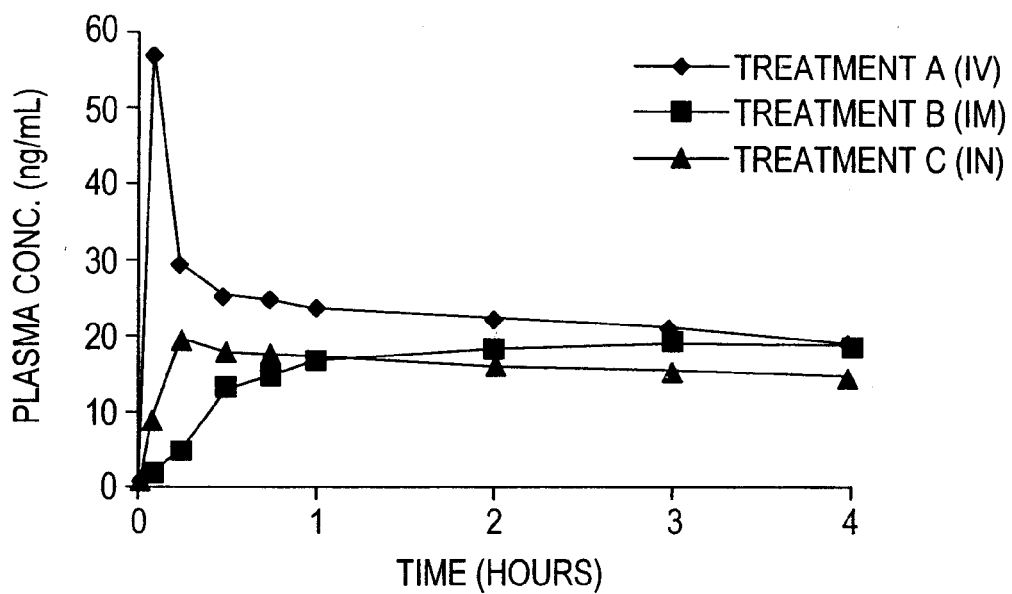

This Application is a Continuation-in-Part of co-pending application Ser. No. 09/569,125, filed May 10, 2000, now abandoned.

FIELD OF THE INVENTION

The invention relates to pharmaceutical drug compositions and preparations of lorazepam. This invention also relates to pharmaceutical drug delivery devices, specifically to devices for the intranasal administration of lorazepam.

BACKGROUND OF THE INVENTION

Lorazepam preparations for the treatment of anxiety-related disorders and to induce sedation have been previously approved by the U.S. Food and Drug Administration ("FDA") and have been long-used for oral, intramuscular and/or intravenous administration. Lorazepam is currently marketed in injectable and tablet formulations. Marketers of these preparations have not sought regulatory approval from the FDA for liquid compositions of the same therapeutic compound for intranasal administration. This is surprising since it is well-known from the literature that the intranasal administration of a pharmacologically active compound generally results in a more rapid bioavailability of the compound, or of its desired active metabolite than if the compound is administered orally. Moreover, the time required to achieve the same concentration of the active compound in the bloodstream e.g., within a period of about thirty minutes after administration, is generally less via the intranasal route compared to oral administration.

It has been reported that, following oral administration, peak plasma concentrations of approximately 25 ng/mL were not observed until approximately 2.4 hours after administration with a bioavailability of 99.8%. (Greenblat, et al., *Journal of Pharmaceutical Sciences*, Vol. 66, No. 1 (1979).) It has also been reported that, following intranasal administration of lorazepam in a Cremophor EL, a non-aqueous vehicle, the time to peak plasma concentration was 1.4 hours with a bioavailability of 51%. (Lau and Slattery, *International Journal of Pharmaceuticals*, 54 (1989) 171–174.)

The intranasal route of administration also provides numerous advantages over intravenous (IV) and intramuscular (IM) injections. One principal advantage of intranasal administration is convenience. An injectable system requires sterilization of the hypodermic syringe and in the institutional setting, leads to concerns among medical personnel about the risk of contracting disease if the they are accidentally stuck by a contaminated needle. Strict requirements for the safe disposal of the used needle and syringe must also be imposed in the institutional setting. In contrast, intranasal administration requires little time on the part of the patient and the attending medical personnel, and is far less burdensome on the institution than injectables. There is no significant risk of infection of medical personnel or others in the institutional setting that is associated with nasal spray devices.

A second important advantage of intranasal administration over IM and IV is patient acceptance of the drug delivery system. Many, if not most, patients experience anxiety and exhibit symptoms of stress when faced with hypodermic injections via the IM or IV routes. In some cases, the after-effects of the injection include burning, edema, swelling, turgidity, hardness and soreness. In contrast, intranasal administration is perceived as non-invasive, is not accompanied by pain, has no significant after-effects and produces the gratification of prompt relief in the patient exhibiting the symptom. This is of particular advantage when the patient is a child. Most people have some familiarity with nasal sprays in the form of over-the-counter decongestants for alleviating the symptoms of colds and allergies that they or a family member have used routinely. Another important consideration is that the patient can self-administer the prescribed dosage(s) of nasal spray. An empty nasal spray device, or one containing a non-medicated solution can be given to the patient to practice the technique for proper insertion, inhalation and activation for self-administration.

In view of the aforementioned advantages and benefits afforded by the intranasal administration, it would be expected that a preparation of lorazepam exhibiting systemic pharmacological activity would presently be available for intranasal administration. This has not occurred, despite the fact that preparations for oral, IM and IV administration have been approved for commercial use for many years.

Despite the remarkable commercial success that has been enjoyed by those drugs that have been made available in intranasal form, in fact, only a very limited number of compounds are commercially available to physicians to prescribe and dispense to their patients in that form.

Furthermore, only one multiple-dose spray device has apparently been approved by the FDA for intranasal administration of an opiate solution that is categorized as a controlled substance. The devices that are presently available exhibit several deficiencies. One spray device intended for multiple uses must be primed before use by expelling a portion of the liquid contents in order to assure that the pump mechanism and delivery tube are filled. Up to seven or eight activations are required to prime the device. It is also indicated that further priming to disperse one or two sprays is to be performed if the device is not used for 48 hours or longer. These procedures necessarily result in the dispenser being overfilled in order to assure that there will be sufficient liquid to deliver the labelled number of doses. It has been found that a substantial volume of the controlled substance often remains in the device, even after the labelled number of doses have been administered. In practice, it has also been found that medical personnel and workers at health care facilities routinely abscond with the dispensers, sometimes after the patient has had only one or a few of the prescribed doses in a multi-dose container. This improper use of controlled substances as so-called "recreational drugs" is well-known among medical facility managers and law enforcement authorities. So far as is presently known, no preventative measures have been reported that are effective in dealing with this problem.

A further problem resides in dispensing to a patient intranasal spray devices with sufficient fluid contents for numerous doses for anxiety control purposes. Because a patient suffering from a disorder and exhibiting anxiety may not act rationally in self-administering a drug for relief of the symptom, there is a potential for overdosing. Moreover, because of the nature and construction of these multiple dose spray devices, medical personnel cannot easily determine the number of doses that have been administered by a simple visual inspection of the device.

Another problem that has recently been identified in clinical studies is the relative inaccuracy of multi-dose intranasal delivery devices that are currently being marketed with opiate solutions for the control of pain. Not only does the average volume of liquid spray actually administered fall about 10% below the purported dosage appearing on the approved label for one such product, significant variations were also observed among a series of administrations by each patient in the study group. Thus, spray devices tested containing an opiate compound classed as a "controlled substance" by the FDA were found to be capable of administering only about 90% by volume of the prescribed dosage, on average, and the dosage actually received by each patient in repeated administrations exhibited substantial significant variations of from 60% to 130% of the claimed label dosage.

OBJECTS OF THE INVENTION

Accordingly, it is a principal object of the invention to provide a novel therapeutic composition of lorazepam and its pharmaceutical by acceptable derivatives for intranasal administration of at least one predetermined volumetric unit dose in the form of a spray by means that delivers one or more therapeutically prescribed unit doses that are highly accurate as to the volume discharged and which leave no significant quantity of the composition in the delivery means.

Another object of the invention is to provide a novel composition comprising lorazepam, a known compound that is approved for oral, IM and/or IV administration, for use in a highly accurate and reproducible intranasal spray delivery system in a single unit-dose or therapeutically prescribed multiple unit-dose.

It is a further object of this invention to provide an improved intranasal dosage composition and method of administration of lorazepam that exhibits a relatively rapid onset, moderate duration of therapeutic activity, minimal side effects, improved bioavailability, ease and safety of administration, and minimal physical discomfort and anxiety to the patient occasioned by administration.

It is another object of this invention to provide an intranasal delivery system for one or more unit doses of novel therapeutic compositions containing lorazepam that permits administration of one or more therapeutically prescribed unit-doses in a medical care facility, such as a hospital, day clinic, or doctor or dentist's office in which the delivery system contains essentially no significant quantity of the therapeutic composition after administration of the single unit-dose or the prescribed number of multiple unit-doses.

It is also an object of the invention to provide the novel and improved combination of a device for intranasal administration and a formulation for lorazepam that meet the requirements for FDA approval.

Yet another object of the invention is to provide such novel lorazepam compositions for intranasal administration in a relatively small and inexpensive, manually operated, self-contained hand-held disposable device that retains essentially no significant quantity of the therapeutic composition after administration of the one or more unit-doses as prescribed.

A further object of the invention is to provide a comprehensive method for providing a novel therapeutic composition for intranasal administration that contains lorazepam in a form that exhibits the same pharmacological activity as lorazepam compositions that are approved for oral, IM and/or IV administration, the intranasal composition being available for delivery in highly accurate and reproducible predetermined unit-doses leaving essentially no significant quantity of the therapeutic composition after administration of the prescribed number of unit-doses.

As used herein, the term "essentially no significant quantity of the therapeutic composition" means none, or a trace amount, or an amount that is so small that it cannot be recovered for a subsequent unintended use or abuse after the prescribed use.

As used herein, the term "spray" means the liquid composition expressed from the device under pressure in the form of an aerosol, a fine mist, liquid droplets, a fine stream, and combinations of two or more of the above forms. It will be understood that the precise form of the composition is dependent upon the viscosity and other physical properties of the composition and the manner in which the manual or other force is applied to the device to discharge the liquid composition. A heterogenous spray is acceptable so long as the sprayed volume is effectively adsorbed by the nasal mucosa.

As used herein, "lorazepam" means lorazepam and its active pharmaceutically acceptable derivatives and metabolites.

SUMMARY OF THE INVENTION

The improved lorazepam composition for intranasal spray administration is prepared by dissolving lorazepam in polyethylene glycol having an average molecular weight of 400, ["PEG 400"] and diluting the solution with propylene glycol to a final composition of about 20% PEG 400 and 80% propylene glycol 2 by volume.

The invention further comprehends the intranasal administration of the lorazepam composition in the form of a spray in a unit-dose of a predetermined therapeutic volume, where substantially all of the predetermined volume of the composition is sprayed from delivery means within a specified narrow range of accuracy, while leaving essentially no significant quantity of the therapeutic composition in the applicator from the unit-dose as administered. The dose is administered principally in the form of liquid droplets, that may be accompanied by a minor proportion of an atomized mist or an aerosol. Application to the nasal mucosa of a subject requiring treatment is consistent with the current therapeutic use of lorazepam for treatment of anxiety-related disorders, and especially useful when acute administration is indicated. Such indications include sedation of agitated and/or demented patients pre-operative surgical/dental sedation and administration to children.

The lorazepam compositions administered in accordance with the method and system of the invention exhibit systemic pharmacological effects following absorption from the nasal mucosa. As will be shown below, the novel pharmaceutical composition provide the lorazepam in a form that is readily absorbable by the nasal mucosa without damaging or irritating the mucosa, or producing an allergic, or other unacceptable reaction in the recipient.

The lorazepam compounds for use in the practice of the invention comprise a pharmacologically acceptable carrier that can be nasally administered with safety over the entire reasonably foreseeable range of prescribed users of the composition. It has been found that the addition of water to the composition reduces the stability of the lorazepam. It is therefore preferred that the liquid composition be non-aqueous. Compatible organic solvents ar preferred.

In one preferred embodiment, the lorazepam composition includes minor proportion of an artificial sweetener. The purpose of the artificial sweetener is to counteract or mask the otherwise bitter taste that the subject can experience if the composition reaches the taste buds. Flavor extracts can also be included in the composition, either in addition to or in place of an artificial sweetener to mask the after taste of the lorazepam composition. The composition preferably has a shelf life in the chosen delivery system of at least six months, and most preferably greater than two years. Optionally, the composition can include one or more preservatives of the type approved for use in pharmaceutical compositions. The preservative is preferably an antioxidant. One preservative that has been found particularly suitable is butylate hydroxytolune, which can be added at the rate of 0.1 mg/mL.

The lorazepam composition of the invention is also compatible with the delivery system. The lorazepam compositions for use in the invention are formulated to deliver the dose within the foreseeable temperature ranges of exposure, e.g., without becoming too viscous to be administered in the proper form by the device, or crystallizing at lower temperatures; and without exceeding the internal pressure limits of the delivery system at higher temperatures.

The predetermined therapeutic volume of the pharmaceutical composition contained in the unit dose is delimited by several parameters, including the capability of the nasal passage to receive and absorb the volumetric quantity of spray; and the solubility of the particular lorazepam in the physiologically and pharmacologically acceptable carrier liquid at the concentration required to achieve the desired effect. The relative safety of administering a given predetermined quantity of lorazepam to classes of patients for anxiety-related disorders or for sedation, whose body weight, age, general health, use of other medications may vary widely and can be determined by methods well known in the art.

Dispensing devices meeting the above criteria and technical specifications have been provided in accordance with the invention by modifying commercially available devices, such as those sold by Pfeiffer of America of Princeton, N.J. and Valois of America, Inc. of Greenwich, Conn. When modified as described below, such devices have the capability of consistently delivering a predetermined volumetric amount of a liquid composition intranasally via a unit-dose dispenser that is manually operable by the patient requiring such intranasal drug administration. These manually operable devices are designed for delivery of a single unit-dose, after which there is essentially significant quantity of the therapeutic composition remaining in the device. The device can thereafter be discarded without concern that others may abuse the controlled substance.

Commercial spray devices can be provided with enough pharmacologically active composition to administer one predetermined unit-dose or two unit-doses ("bi-dose"), each with a high degree of accuracy and reproducibility for the device and among a plurality of such commercially manufactured and filled devices.

In accordance with the invention, the orifice of a commercial spray applicator was enlarged and the swirl chamber is retained in order to produce a spray that is principally in the form of liquid droplets that coat the nares. A minor proportion of the product may be in the form of a mist or aerosol. The size of the orifice is optimized in relation to the viscosity of the lorazepam composition.

Devices that are suitable for use in the practice of the invention are fabricated from a variety of polymeric materials, and can also include glass or polymer containers for the liquid lorazepam composition and metal components, preferably of stainless steel, that form elements of the delivery system. Such devices are compact, relatively inexpensive and can be discarded after the prescribed use. In a preferred embodiment, the container and its sealing means are sterilizable; most preferably, the entire device is constructed from materials that can be sterilized.

The preparation of the lorazepam composition and its aseptic filling into containers and the assembly of the filled containers in the spray devices must be completed under aseptic conditions since the lorazepam cannot withstand terminal sterilization without decomposition. Spray devices can be sterilized before filing, along with the intended packaging, employing methods and technology that are well known in the art.

BRIEF DESCRIPTION OF THE DRAWINGS

The novel features and other advantages of the present invention, in addition to those mentioned above, will become apparent to those skilled in the art from the following detailed description and in conjunction with the accompanying drawings, in which:

FIG. 1 is a graphic representation of the concentration of lorazepam in blood plasma versus time for IV, IM and IN doses; and FIG. 2 is a graphic representation of the data of FIG. 1 over a longer time period.

DETAILED DESCRIPTION OF THE PREFERRED EMBODIMENT

A suitable liquid composition for use in a spray device for intranasal administration includes a solvent in which the desired concentration of lorazepam can be attained to provide the desired unit-dose in a total sprayed liquid volume that can be delivered by the device and accommodated and absorbed by the subject's nasal mucosa. Lorazepam is insoluble in water. A commercially available injectable composition approved by the FDA and sold by Wyeth Laboratories under the brand name Ativan®, includes 2 mg of lorazepam in 0.18 mL of polyethylene glycol 400 in propylene glycol with 2.0% benzyl alcohol as a preservative. This composition was not acceptable for intranasal spray administration because benzyl alcohol is irritating to the mucosa.

A suitable composition for use in the invention was prepared as follows.

Lorazepam was formulated in a liquid composition for use in the practice of the invention. Since lorazepam is insoluble in water, the lorazepam was dissolved in polyethylene glycol having an average molecular weight of about 400 ("PEG400"), and the solution diluted with propylene glycol. In order to provide for shelf-life stability over a period of up to six-months under typical conditions, a preservative can be added. In a preferred embodiment, an artificial sweeter is also dissolved in the composition. The final composition was as follows:

| | |
|---|---|
| lorazepam | 10.0 mg |
| polyethylene glycol 400 | 0.18 mL |
| propylene glycol | 0.809 mL |
| butylate hydroxytolune | 0.1 mg |
| saccharin (powder) | 1.0 mg |

The lorazepam is preferably prepared in the form of a single or unit-dose nasal spray for intranasal administration by a precision dosage manually-activated pump. Each 1 ml of nasal spray solution is preferably formulated to contain 10 mg lorazepam. In a preferred delivery system, each actuation of the nasal spray pump delivers 0.1 ml of this 10 mg/ml hm solution constituting a 1 mg dose. A smaller dose of the lorazepam HCl can be administered to children.

As will be understood by those familiar with the art, dosage forms at lower concentrations of lorazepam can be prepared for administration based upon the patient's lower body weight, as in the case of children or adults of substantially smaller size. The nasal spray solution has a pH in the range of from about 3 to about 7, with a pH of about 5 being preferred.

The lorazepam composition was placed in containers adapted for use with modified Pfeiffer dispensers identified by model/part numbers as 52020/BSK 7482. The intranasal applicators of the prior art are modified by increasing the size of the discharge orifice in nose piece to about 0.07 mm from about 0.05 mm in diameter (which is typical for an aqueous solution), i.e., a 40% increase in diameter. This increase is necessary to accommodate the higher viscosity of the composition of the invention. The swirl chamber of the prior art precision spray dispenser can be retained. The applicator components are sterilized by methods well known in the art. As will be understood by those of ordinary skill in the art, other changes in the design and/or construction of the spray dispenser can be made to accommodate and discharge the more viscous composition of the invention.

The lorazepam nasal spray applicators are preferably stored at temperatures in the range of 2°–8° C. (36°–48° F.) and are protected from light to provide for maximum shelf life. If the applicator body is not transparent, visual inspection of the drug product for signs of deterioration is not possible and attention to the expiration date and storage conditions is important. The optional inclusion of a preservative will serve to extend the shelf life, as will storage under refrigeration. In the last case, the products and dispenser should be brought to room temperature before administration. Any expired product is discarded in the appropriate manner.

A formulation of lorazepam for intranasal administration was prepared as described above under aseptic conditions in the form of a liquid composition at a concentration of 1.0 mg of lorazepam in 0.1 mL. The composition was used to fill the required number of single-dose, metered sprayers commercially produced and sold by Pfeiffer of America, Inc., each of which sprayers first having been modified as described above. The filling of the containers and their assembly is completed under aseptic conditions since the lorazepam composition cannot withstand the heat of sterilization.

Each subject received a single spray in each nostril for a total of 2.0 mg. A 2.0 mg dose is preferred as being within common, safe and labeled doses prescribed. Commercially available lorazepam was purchased for IM and IV administration. The product was Ativan® Injection for parental administration sold by Wyeth Laboratories, (a Wyeth-Ayerst Company.) Each mL of Ativan® Injection is formulated with 2 mg of lorazepam in 0.18 mL PEG400 in propylene glycol with 2.0% benzyl alcohol as a preservative. The IV doses were diluted according to the label instructions by adding one mL of water.

Each of the applicators was weighed prior to use and after use. Qualified medical personnel took the respective applicators to subjects in a clinical setting; one dose was administered up each nostril, after which the applicator was recovered for weighing. Each subject used two Pfeiffer unit dose spray devices, both of which were discarded following the post-use weighing. The IV doses were administered through antecubital veins on the arm opposite to the arm from which samples were taken, injecting the solution over about five minutes. Syringes were weighed before and after administration. Further details of the protocol, and the results of these studies of the methods and system of the invention and the comparative prior art method follow.

Unit-Dose:

A statistical comparison of dose 1 and dose 2 for the Pfeiffer unit dose delivery system was done using a paired t-test. Analysis of the data for normally functioning devices indicated that the difference between the mean sprays of the two applications using the Pfeiffer device was not statistically significant. (This analysis excluded data from one of the devices that malfunctioned.)

Investigational Methods

A clinical study was undertaken for the purposes of (1) to assessing the absolute bioavailability of lorazepam by comparing the pharmacokinetics of 2.0 mg lorazepam administered by intranasal (IN) and intravenous (IV) routes; and (2) to compare pharmacokinetic parameters via IN administration to intramuscular (IM) and intravenous administration. This was undertaken as a single-dose, open-label, three-way crossover, randomized, pilot bioavailability study of lorazepam comparing intranasal administration in healthy human volunteers.

Twelve healthy non-smoking subjects (six male and six female) between the ages of 18 and 35 years were initially selected for this inpatient study. One subject left the study and one subject received delayed doses. Study participants were selected based on inclusion/exclusion criteria, history and physical exam, laboratory tests, and other customary procedures.

The subjects were within ±20% of ideal body weight and no history of allergies, acute or chronic nasal symptoms, significant nasal surgery or abnormalities were reported.

Eleven of the twelve subjects completed the study according to the protocol. Each of the subjects received 3 doses of 2 mg of lorazepam on three separate occasions. No clinically significant protocol violations occurred during this study. The inclusion criteria mentioned abstinence from prescription and non-prescription drugs prior to and during the study, and any medications taken in the 14 days before the study and during the study were noted. Subjects abstained from alcoholic and caffeine-containing beverages for 48 hours before the dosing period and during the study.

Clinical Trials

Study Drug Formulation

Lorazepam for intranasal administration was supplied by the University of Kentucky College of Pharmacy. Lorazepam for intravenous administration ("IV") was supplied as Ativan® 1 mg/mL for subjects 1, 3, 8, and 9 on the first day and for subjects 2, 4, 5, 6, and 7 on the second study day. Lorazepam for intramuscular administration ("IM") was supplied as Ativan® 2 mg/mL for subjects 2, 4, 5, 6 and 7 on first study day and for subjects 1, 3, 8 and 9 on the second study day. Free base content was 1.77 mg or 88.7% of stated lorazepam strength (from molecular weights: 321.8−36.46=285.34, 285.34/321.8=88.7%) To summarize, the dosages for each of the three routes of administration were as follows:

Treatment A: 2.0 mg intravenous lorazepam;

Treatment B: 2.0 mg intramuscular lorazepam; and

Treatment C: 2.0 mg intranasal lorazepam solution

Study Drug Administration

Drug administration occurred at approximately 0800 hours following overnight fasting. Subjects were allowed up to 360 mL of juice or soft drink one hour before each dose, but were not allowed to eat for one hour after their dose.

Safety Measures

Weight, blood pressure, and pulse were measured prior to dosing and at the end of the study. Blood pressure and pulse rate were measured with the subjects seated in an upright position before any corresponding blood sample was collected. Blood pressure and pulse rate were measured and recorded on the same arm throughout the study at 0 (pre-dose) and 30 minutes, 1, 2, 4, 8, and 16 hours.

The three treatments were separated by one-week wash-out period. The subject (#02) whose doses were delayed received the final dose within one month of the first dose, was dosed with the other subjects during their first and third periods and received the final treatment two weeks later. She was dosed in the treatment order to which she was randomized.

Clinical Adverse Events

Spontaneously reported adverse events were recorded by the subjects throughout the study; adverse events were also elicited by nondirected interviews.

Sample Collection and Handling

Blood samples for the three treatments were collected from each subject according to the following schedule: 0 (pre-dose), 5, 15, 30 and 45 minutes, and 1, 2, 3, 4, 8, 12, 18, 24 and 36 hours following lorazepam administration. The beginning of the IV administration was considered time zero. After collection, the blood was centrifuged in a refrigerated centrifuge at 4° C. to separate the plasma and the cells, and the plasma was transferred to polypropylene tubes. The plasma was stored at approximately −70° C. at the study site until shipped to an independent analytical service. The plasma was maintained frozen during shipping and upon arrival at the remote analytical facility, the samples were stored at approximately −20° C. until analyzed.

Bioanalytical Methods

LC/MS/MS Assay for Lorazepam

The sample analysis using an LC/MS/MS assay was performed by an independent service in accordance with established protocols. The analytic range for the lorazepam method was 0.10 ng to 25.00 ng/mL using 1.0 mL of human plasma. Concentrations less than 1.10 ng/mL were reported as below quantitation limit (BQL). Samples with concentrations greater than 25 ng/mL were reanalyzed using a dilution so that the assayed concentration was within the range of 0.10 ng to 25.00 ng/mL.

Pharmacokinetic Methods

Plasma concentration versus time date for lorazepam were analyzed using noncompartmental pharmacokinetic methods. Pharmacokinetic parameters were determined using standard noncompartmental methods with log-linear least square regression analysis to determine the elimination rate constants (WinNonlin, Pharsight Corp., Palo Alto, Calif.). The areas under the concentration versus time curves from time zero to infinity ($AUC_{0-\infty}$) were calculated by a combination of the linear and logarithmic trapezoidal rules, with extrapolation to infinity by dividing the last measurable serum concentration by the elimination rate constant ($\lambda_z$) (Proost, 1985). Values for the maximum concentration ($C_{max}$) and time to $C_{max}$ ($T_{max}$) were determined by visual inspection of concentration versus time data for each subject. The elimination half-life was determined from $0.693/\lambda_z$. The absolute bioavailability (F) for the IN and IM dosage forms, assuming equal 2 mg doses, was determined by $F=AUC_{IN,0-\infty}/AUC_{IV,0-\infty}$ for the IN dose and $F=AUC_{IM,0-\infty}/AUC_{IV,0-\infty}$ for the IM dose. Clearance (CL for IV and CL/F for IN and IM doses) was determined by dividing the dose by $AUC_{0-\infty}$. Volume of distribution at steady state and for elimination ($V_{ss}$ and $V_z$) were determined by moment curves (Gibaldi and Perrier, 1982).

TABLE 1

Mean (CV as a %) pharmacokinetic parameters following administration of 2 mg intravenous (IV infusion over 5 min), intranasal (IN) and intramuscular (IM) lorazepam doses in 11 healthy volunteers.

| Parameter | 2 mg IV | 2 mg IM | 2 mg IN |
|---|---|---|---|
| $T_{max}$ (hrs*) | 0.1 | 3.0 | 0.5 |
| | (0.083 to 1.017) | (0.5 to 8.017) | (0.25 to 2) |
| $C_{max}$ (ng/mL) | 47.57 (57.8) | 22.58 (28.9) | 21.38 (24.3) |
| $t_{1/2}$ (hr) | 16.6 (27.3) | 17.4 (38.1) | 18.5 (28.3) |
| $AUC_{0-4}$ (ng · hr/mL) | 386.8 (19.4) | 372.8 (16.4) | 288.0 (25.4) |
| $AUC_{0-\infty}$ (ng · hr/mL) | 500.8 (30.8) | 506.2 (33.7) | 393.5 (38.0) |
| CL or CL/F (L/hr) | 4.3 (27.0) | 4.3 (28.5) | 5.7 (31.8) |
| $V_{SS}$ (L) | 93.2 (11.9) | — | — |
| $V_Z$ or $V_Z/F$ (L) | 97.8 (15.2) | 99.2 (10.8) | 140.1 (16.8) |
| F (%) | assume 100% | 100.9 (10.2) | 77.7 (11.1) |

*median and range given for $T_{max}$

Table 1 is a summary of pharmacokinetic data for the three doses. Absorption of lorazepam following IN administration was rapid as indicated by the fact that concentrations were detected in all subjects within five minutes after the IN administration. The median $T_{max}$ values were 30 minutes and three hours for the IN and IM doses, respectively. On average, 0.1091 g (CV 5.6%, n=21) was dispensed from the individual spray pumps as determined by the difference in the pre- and post-weights. (This data excludes one malfunctioning device of the 22 devices used in this study.) The mean plasma concentration versus time curve profiles for the IV, IM and IN doses are shown in FIG. 1. Plasma concentrations were still detectable 36 hours after administration.

Figure 2:
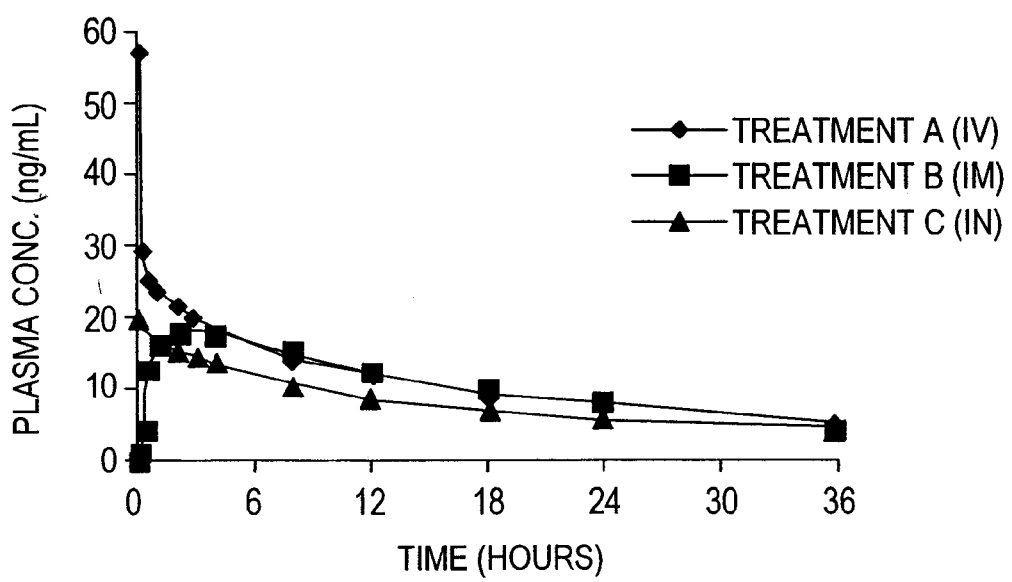

FIGS. 1 and 2 are plots of the mean (n=11) plasma lorazepam concentration versus time graphs following three treatments: (A) 2.0 mg lorazepam by five minutes IV infusion, (B) 2.0 mg lorazepam IN dose and (C) 2.0 mg lorazepam IM dose. FIG. 1 shows the results over the period following administration; FIG. 2 is the same data for the 36 hours following administration.

Safety Results

Results of the clinical measurement of vital signs and body weight exams were recorded and nasal exams were performed. A review of this data failed to reveal any clinically significant safety concerns. There were no serious adverse events and no subjects were discontinued due to adverse effects. Subjects commented that they experienced a mild bad taste immediately after the IN dose. Any safety concerns associated with IN are similar to those associated with IV administration.

Detailed nasal examination demonstrated no pathology of the naso-pharynx after single administration of the lorazepam formulations.

Pharmacokinetic Results

The plasma lorazepam concentrations and actual collection times for each of the 11 subjects was tabulated and plasma concentration-time curves for each of the 11 subjects were prepared. The mean concentration-time curves of FIGS. 1 and 2 are representative for most subjects (mean data tabulation). FIG. 1 is a plot of the mean (n=11) lorazepam concentration versus time graphs following IV, IM and IN doses of 2 mg lorazepam during the 4 hours after dose; FIG. 2 is the same data plotted for 36 hours after the dose.

Noncompartmental pharmacokinetic analysis was used to evaluate the plasma concentration versus time curves of lorazepam following single 2.0 mg doses of lorazepam by intravenous (IV), intramuscular (IM), and intranasal (IN) routes. Individual plasma lorazepam concentration versus time profiles for all subjects were recorded; number of time points used to estimate the elimination rate constant were also recorded; and a complete listing of individual and mean pharmacokinetic parameters for all 11 subjects was recorded. Table 1 is a summary of the descriptive statistics for lorazepam pharmacokinetic parameters.

Rapid absorption of lorazepam was observed after the IV and IN doses. The $T_{max}$ values were approximately 9 and 18 minutes, on average, for the IM and IN doses, respectively. The mean $T_{max}$ for the IV infusion was not the first blood sample after the end of the infusion for two reasons. The peak concentration after the IV dose in one subject was not at the first blood sample after the end of the IV infusion, but at the next time point. In the case of Subject 4, acquiring the blood sample immediately following the IV infusion was delayed resulting in the mean $T_{max}$ being affected. As expected, the lorazepam $C_{max}$ and AUCs were significantly higher after IM and IV administration compared to IN administration. Mean plasma half-lives and clearance after correcting for bioavailability, were similar for all three treatments.

The arithmetic mean value of absolute bioavailability of lorazepam (11 subjects) for the IN formulation is 78%. The plasma levels were comparable to those of the IM dose.

From the above, it will be understood that a novel composition and method is provided for the safe and controlled intra-nasal administration of precise doses of lorazepam in accordance with a medically prescribed regimen.

What is claimed is:

1. A pharmaceutical composition for intranasal administration to a mammal that produces a sedative-anxiolytic physiological response in the mammal, the composition consisting essentially of:
   lorazepam;
   polyethylene glycol and propylene glycol as a solvent-carrier for the lorazepam; wherein the polyethylene glycol constitutes from about 15% to about 25% by volume and the propylene glycol constitutes from about 75% to about 85% by volume of the composition; and
   a sweetener,
   wherein the composition forms a spray when discharged from a manually actuated spray device.

2. The composition of claim 1, wherein the polyethylene glycol has an average molecular weight of about 400.

3. The composition of claim 1, wherein the polyethylene glycol constitutes about 20% by volume and the propylene glycol about 80% by volume of the composition.

4. The composition of claim 3, wherein the solvent-carrier is polyethylene glycol having an average molecular weight of about 400.

5. The composition of claim 3, wherein the lorazepam is present in the composition at a concentration of 1.0 mg/0.1 mL.

6. A sprayable liquid pharmaceutical composition for intranasal administration in the form of at least one unit-dose to a mammal for the purpose of producing a sedative-anxiolytic response in the mammal, the composition consisting essentially of:
   lorazepam;
   polyethylene glycol and propylene glycol as a solvent for the lorazepam; wherein the polyethylene glycol constitutes from about 15% to about 25% by volume and the propylene glycol constitutes from about 75% to about 85% by volume of the composition, a sweetener, and
   a preservative,
   wherein the lorazepam is present in the liquid composition at a concentration of about 1.0 mg/0.1 mL.

7. The composition of claim 6, wherein the polyethylene glycol has an average molecular weight of about 400.

8. The composition of claim 7, wherein the ratio of polyethylene glycol to propylene glycol is about four-to-one.

9. The composition of claim 7, wherein the solvent constitutes about 80% by volume and the propylene glycol about 18% by volume.

10. The composition of claim 6, wherein the sweetener is selected from the group consisting of saccharin and aspartame.

11. The composition of claim 10, wherein the sweetener is saccharin.

12. The composition of claim 6, wherein the preservative is butylated hydroxytoluene.

13. A method of treating a mammal exhibiting symptoms of anxiety-related disorders, said mammal requiring treatment, the method comprising the steps of:
   a. providing an intranasal spray delivery device;
   b. filling the delivery device with a sprayable liquid composition, the liquid composition consisting essentially of:
      lorazepam, polyethylene glycol and propylene glycol as a solvent-carrier for the lorazepam; wherein the polyethylene glycol constitutes from about 15% to about 25% by volume and the propylene glycol constitutes from about 75% to about 85% by volume of the composition, a sweetener, and
   c. administering a predetermined measured dose of the liquid lorazepam containing composition intranasally to the mammal requiring treatment by spraying the liquid composition droplets from the delivery device into at least one of the mammal's nostrils.

14. The method of claim 13, wherein the dose is administered by manually activating the delivery device.

15. The method of claim 13, wherein the predetermined dose is administered by spraying the lorazepam-containing composition first in one nostril and then in the other.

16. The method of claim 13, wherein the mammal is an adult human and the predetermined dose is two Mg of lorazepam.

17. The method of claim 13, wherein the sprayable liquid composition is prepared by dissolving lorazepam in the solvent carrier and adding the lorazepam in the solvent carrier to the delivery device under aseptic conditions.

18. The method of claim 13 which includes the further step of sterilizing the delivery device before addition of the liquid composition.

19. A pharmaceutical composition for intranasal administration consisting essentially of:
   lorazepam;
   polyethylene glycol and propylene glycol; wherein the polyethylene glycol constitutes from about 15% to about 25% by volume and the propylene glycol constitutes from about 75% to about 85% by volume of the composition;
   and a sweetener.

20. A composition according to claim 19, wherein the polyethylene glycol has an average molecular weight of about 400.

21. A composition according to claim 19, wherein the polyethylene glycol constitutes about 20% by volume and the propylene glycol about 80% by volume of the composition.

22. A composition according to claim 19, wherein the lorazepam is present in the composition at a concentration of 1.0 mg/0.1 ml.

23. The composition of claim 19, wherein the sweetener is saccharin, aspartame or combination thereof.

24. A pharmaceutical composition for intranasal administration consisting essentially of:

lorazepam;

polyethylene glycol and propylene glycol; wherein the polyethylene glycol constitutes from about 15% to about 25% by volume and the propylene glycol constitutes from about 75% to about 85% by volume of the composition;

a sweetener, and a preservative.

25. A composition according to claim 24, wherein the sweetener is saccharin, aspartame or combination thereof.

26. A composition according to claim 24, wherein the preservative is butylated hydroxytoluene.

27. A pharmaceutical composition for intranasal administration consisting essentially of:

lorazepam 10.0 mg;

polyethylene glycol 400 0.18 mL;

propylene glycol 0.09 mL;

butylated hydroxytoluene 0.1 mg; and saccharin 1.0 mg.

28. A method of treating a mammal suffering from anxiety comprising intranasally administering a pharmaceutical composition consisting essentially of:

lorazepam;

polyethylene glycol and propylene glycol; wherein the polyethylene glycol constitutes from about 15% to about 25% by volume and the propylene glycol constitutes from about 75% to about 85% by volume of the composition;

a sweetener; and a preservative, wherein the composition achieves a plasma lorazepam $C_{max}$ of at least 21 ng/ml when administered intranasally.

* * * * *